United States Patent [19]

Compans et al.

[11] Patent Number: 4,790,987
[45] Date of Patent: Dec. 13, 1988

[54] VIRAL GLYCOPROTEIN SUBUNIT VACCINE

[75] Inventors: Richard W. Compans, Helena; Ranjit Ray, Birmingham, both of Ala.

[73] Assignee: Research Corporation, New York, N.Y.

[21] Appl. No.: 798,536

[22] Filed: Nov. 15, 1985

[51] Int. Cl.[4] .............................................. A61K 39/12
[52] U.S. Cl. ...................................... 424/89; 424/88; 530/391
[58] Field of Search .................................... 424/89, 88

[56] References Cited

U.S. PATENT DOCUMENTS

| | | | |
|---|---|---|---|
| 4,196,191 | 4/1980 | Almeida | 424/89 |
| 4,235,877 | 11/1980 | Fullerton | 424/92 |
| 4,396,630 | 8/1983 | Riedl et al. | 424/88 |
| 4,522,809 | 6/1985 | Adamowicz et al. | 424/89 |
| 4,565,696 | 1/1986 | Heath et al. | 424/85 |

OTHER PUBLICATIONS

Hsu et al., *Virology*, 95, 1979, pp. 476–491.
Macfarlan CA vol. 105, 1986, #59141m.
Kravtsov et al., CA #101, 1984, #86035d.
Visser et al., CA.#103, 1985, #59294x and 59295y.
Lerner et al., Vaccines 85, 1985, pp. 315 and 185.
Chanach et al., *Modern Approaches to Vaccines*, 1984, pp. 373–377.
Synthetic Peptides as Antigen, 1986, pp. 198, 291.

*Primary Examiner*—Ronald W. Griffin
*Assistant Examiner*—Garnette D. Draper
*Attorney, Agent, or Firm*—Scully, Scott, Murphy & Presser

[57] ABSTRACT

The present invention relates to a vaccine composition useful in preparation of virus-caused disease comprising as its active agent at least one immunogenically effective amount of immunogenic viral envelope glycoprotein complexed with a lipid.

19 Claims, 3 Drawing Sheets

VIRAL GLYCOPROTEIN SUBUNIT VACCINE

FIELD OF THE INVENTION

The present invention relates to a vaccine composition for prevention of viral infections. More specifically, it relates to a vaccine composition comprising virus subunits as the active component, for inoculation of hosts susceptible to viral infection, especially mammalian species, including man. It also relates to a method for preparing these vaccine compositions.

BACKGROUND OF THE INVENTION

A wide variety of different viruses are responsible for causing viral infections of varying severity in animals and man. Because of the large number of potentially serious or widespread epidemics, e.g., influenza, resulting from viral infections, methods are constantly being sought for either prevention or cure of the diseases caused by these entities. The difficulty in finding cures for diseases caused by entities about which so little is understood has tended to lead scientists to concentrate on the preventive aspects of viral disease. Along these lines, development of vaccines which can prevent or lessen the symptoms of viral infection has long been a goal of immunologists. Two principal types of vaccine are currently enjoying the most widespread use. One type is the attenuated live virus type of vaccine in which the virus has been rendered avirulent but not killed, either through a serial passage through a number of host cells, or, less commonly, by some form of genetic attenuation. While this type of vaccine has achieved a measure of success, the primary drawback is that the attenuated virus may revert back to its virulent state while living in the host's body. Another type of vaccine consists of virus particles unactivated by formalin or other chemical or physical treatment. The principle behind the use of the killed viruses is that, in theory, the viral antigens which are responsible for producing the required protective immune response remain intact while the ability of the virus to replicate in the host has been destroyed by the formalin treatment. This formalin-inactivated type of vaccine is probably the most common on the market today; however, despite the widespread use of this technique of vaccine preparation the resulting products are really not very effective because the formalin treatment often chemically alters the antigen in some way so as to render it less potent in eliciting an immune response in the host.

In an attempt to circumvent the problems encountered with the two commonly used vaccine types, considerable effort has been put into attempting to isolate the antigenic components of the viral coat. Theoretically, the isolated antigens would be capable of stimulating the host's immune system even in the absence of the other parts of the virus; at the same time, there would be no live virus present, and hence no possibility of infection. The viral antigens must, of course, be isolated in a manner which does not alter them chemically, and allows the antigenicity to be fully retained. Some of the most useful components in this regard are the glycoproteins which make up part of the viral envelope. Glycoproteins are found as structural and/or functional elements of virtually all viruses, and are frequently highly antigenic. A number of glycoprotein preparations derived from viral envelopes have been suggested as possible active components for vaccine compositions. For example, U.S. Pat. No. 4,470,967 describes vaccine preparations which are made by complexing viral glycoprotein with a lectin, the latter element acting as an adjuvant. A number of references, e.g., as described in U.S. Pat. Nos. 4,344,935, or 4,356,169 or Morein et al., J. Gen. Virol. 64: 1557-1569, 1983, utilizes a method of preparation of paranfluenza glycoprotein compositions in which the viral glycoprotein HN and F are solubilized with a detergent, to extract them from the viral envelope, followed by some method of phase separation in order to remove the detergent and lipids. The latter procedures claim to produce a glycoprotein subunit which is not only substantially detergent free, but also lipid free. The latter type of highly purified glycoprotein is currently touted as the preferred type of active agent for potential use as commercial vaccine. However, at present no vaccine composition containing such a purified glycoprotein preparation has been made commercially available. To a large extent this may be due to the difficulty in preparation of the glycoprotein subunit: removal of the detergent and lipid is usually achieved by separation on a sucrose gradient, a tedious procedure which is difficult to accomplish on a scale large enough to make commercial production feasible.

It has now been unexpectedly discovered that a new method of preparation of viral subunit vaccines produces an antigenic product which is capable of eliciting an antibody response in the inoculated individual which is far superior to that obtained with the commonly used formalin-inactivated viral vaccine preparations. Furthermore, it is also simpler to prepare the isolated subunit of the present invention, since, rather than consisting of a purified, lipid-free, protein micelle as a number of the previous vaccines do, the present preparation is composed of a glycoprotein-lipid complex vesicle, which has the advantage of not requiring the removal of the normally present lipid from the solubilized glycoprotein. The fact that a glycoprotein-lipid complex could show such exceptional ability to confer immunity is particularly surprising, since conventional wisdom teaches that lipids are non-antigenic and thus their presence in a vaccine composition would be thought to reduce the efficiency, or even interfere significantly, with the ability of the vaccine composition as a whole to induce immunity. The present subunit vaccine active component is prepared, as are many of the known subunit compositions, by detergent extraction; however, a major distinction exists in that the detergent used in the extraction process is a dialyzable detergent. The specific use of a dialyzable detergent allows the relatively simple purification even on a large scale, by dialysis, of the glycoprotein-lipid complex of the present invention. Thus, the present preparations not only have the advantage of being easier to prepare than the proposed glycoprotein vaccine compositions in the literature, but also are far more effective than the currently available commercial products.

BRIEF DESCRIPTION OF THE INVENTION

The present invention provides a vaccine composition useful in prevention of virus-caused disease comprising as its active agent an immunogenically effective amount of at least one antigenic viral envelope glycoprotein complexed with a lipid. The present invention also provides a method of preparing a vaccine composition useful in prevention of virus-caused disease, which comprises dialyzing a solution containing dialyzable detergent, at least one solubilized antigenic glycoprotein, and solubilized lipid, for a period of time sufficient to remove the detergent, so that an antigenic glycoprotein-lipid complex is formed. Also provided are monoclonal antibodies to parainfluenza glycoproteins, and a method of isolating glycoproteins employing these monoclonal antibodies as immunoadsorbents.

DETAILED DESCRIPTION OF THE FIGURES

Figure 1:
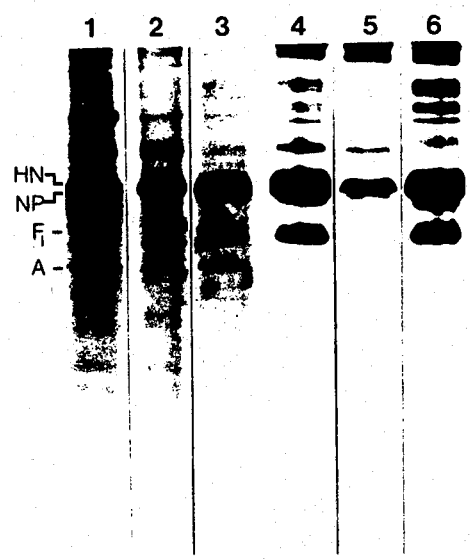

FIG. 1 Solubilization of envelope constituents from PI3 virus with octylgucoside. $^3$H-leucine-labeled PI3 virus (lane 1) was treated with octylglucoside and the detergent insoluble (lane 2) and soluble (lane 3) fractions were analyzed by SDS-PAGE. The glycoprotein profiles of $^3$H-glucosamine labeled PI3 virus (lane 4), its detergent insoluble (lane 5) and soluble (lane 6) fractions were analyzed similarly. The incorporation of $^3$H-label into some polypeptides in lane 5 may reflect metabolic conversion into amino acid precursors.

Figure 2:
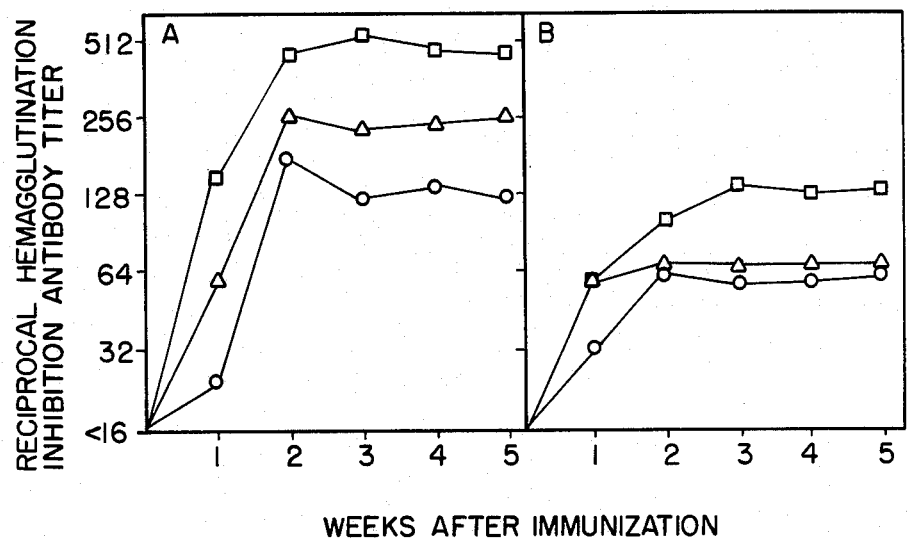

FIG. 2 Hemagglutination inhibition titers of hamster sera collected at weekly intervals following single subcutaneous immunization with three different doses of viral envelope proteins (panel A) or corresponding amount of formalin inactivated virus proteins (panel B). Titers are expressed as the mean value from nine animals immunized with 20 μg (0—0), 40 μg (Δ—Δ) and 80 μg (□—□) of envelope proteins or 60 μg (0—0), 120 μg (Δ—Δ) and 240 μg (□—□) of formalin-inactivated virus proteins. Titers of preimmune and three unimmunized control hamster sera were <16.

Figure 3:
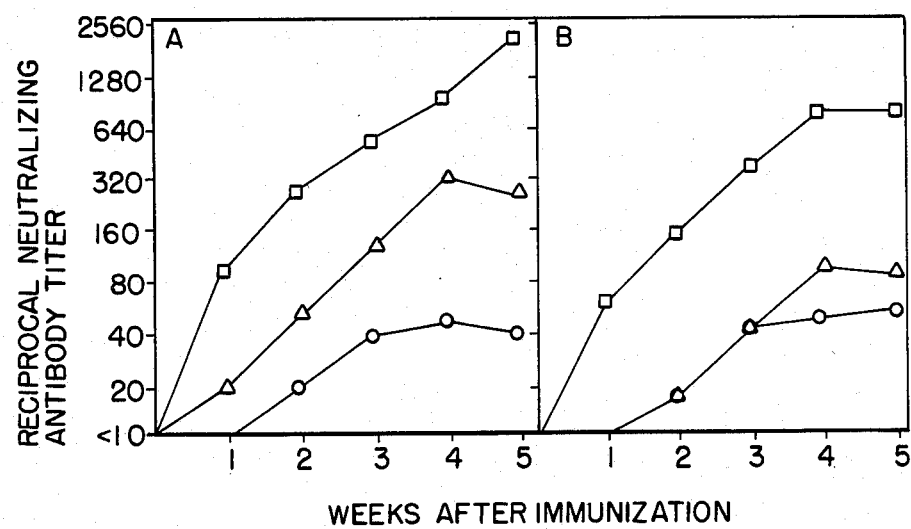

FIG. 3 Neutralizing antibody titers of hamster sera collected at weekly intervals following a single subcutaneous immunization with three different doses of viral envelope proteins (panel A) or corresponding amounts of formalin-inactivated virus proteins (panel B). Titers are expressed as the mean value from nine animals immunized with 20 μg (0—0), 40 μg (Δ—Δ) and 80 μg (□—□) of envelope proteins or 60 μg (0—0), 120 μg (□—□) and 240 μg (□—□) of formalin-inactivated virus proteins. Titers of preimmune and three unimmunized control hamster sera were <10.

Figure 4:
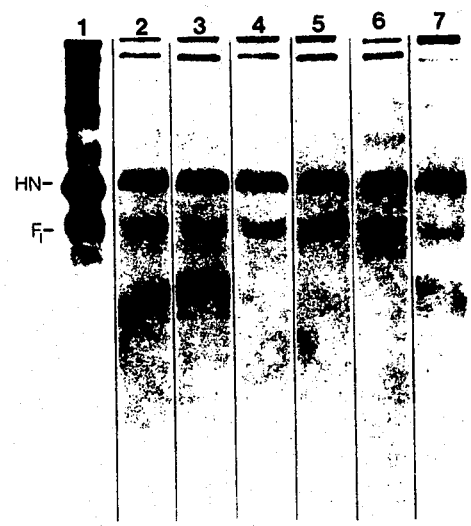

FIG. 4 Immune precipitation of $^3$H-glucosamine-labeled purified virus with representative hamster sera and bronchial washings. Glycoprotein profiles of $^3$H-glucosamine labeled virus (lane 1) and immune precipitations with different sera from hamsters immunized with 80 μg envelope proteins (lanes 2 and 3) or 240 μg of inactivated virus proteins (lanes 4 and 5) were analyzed by SDS-PAGE. Immune precipitates with bronchial washings after challenge infection of hamsters immunized with 80 μg envelope proteins (lane 6) or 240 μg inactivated virus proteins (lane 7) were analyzed similarly.

Figure 5:
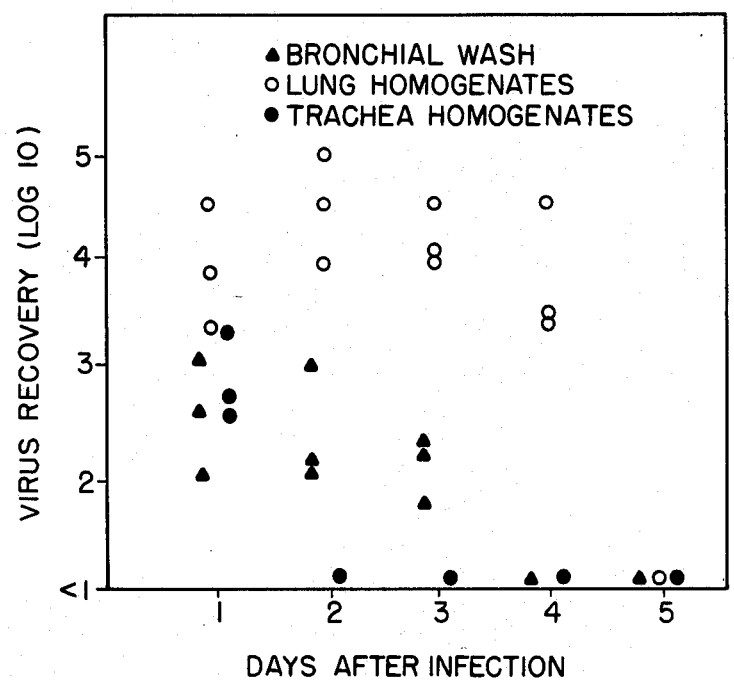

FIG. 5 Replication of PI3 virus in hamsters. Virus recovery from bronchial washing (total pfu) and lungs or trachea (pfu/gm) from three experimental animals are shown.

DETAILED DESCRIPTION OF THE INVENTION

The vaccine preparations of the present invention comprise, as their active agent, an immunogenically effective amount of at least one viral envelope glycoprotein subunit-lipid complex. Throughout the present specification and claims, the terms "immunogenic" and "antigenic" may be used interchangeably, and are intended to mean having the ability to stimulate a protective immune response in the host organism.

Substantially all lipid containing viruses have at least one, and possibly 2 or more, glycoproteins on the surface of the viral envelope, and as previously noted these glycoproteins are, more often than not, antigenic to some extent. Thus, any lipid-containing virus which has an antigenic glycoprotein component provides suitable material for the present vaccine. The lipid component of the glycoprotein-lipid complex is in fact a contribution to the viral envelope from the host cells in which the virus is produced. The lipids are incorporated into the envelope, along with the virus-specified proteins, during envelope assembly in the host cell. The lipids are then extracted simultaneously, because of their solubility in the detergent, with the glycoprotein; upon dialysis, the glycoprotein and lipids spontaneously form discrete complexes/or vesicles. Rather than being an undesirable component of the resulting glycoprotein subunit vaccine as would be expected, the associated lipids may enhance the immunogenicity of the preparation as a whole by acting as an adjuvant. The ability to form the antigenic lipid-glycoprotein vesicles is a function of the chemical nature of glycoproteins and lipids in general, and thus is not restricted to any specific type of glycoprotein or lipid.

Among the better known viral glycoproteins which are generally recognized as being antigenic are two types which are known generically as receptor-binding glycoproteins and fusion glycoproteins. These are defined by their function in the process of host cell infection, and may be known by different specific names in different viruses; at least one, and frequently both, are present in such important disease causing agents as herpes virus, influenza virus, paramyxoviruses, rabies virus, and human T-cell lymphotropic viruses, -the etiologic agent of AIDS.

Particularly well-characterized are the receptor-binding type and F fusion type glycoproteins, possessed by all members of the paramyxovirus group; among these are included the parainfluenza viruses, measles virus, mumps virus, respiratory syncytial virus, Newcastle disease virus, and Sendai virus. In parainfluenza viruses, these glycoproteins are known as F and HN, and are believed to be responsible for initiation of infection (F) and hemagglutination and neuraminidase activities (HN) by the virus. Each of these glycoproteins is known to be highly antigenic, and thus are particularly favored for use in vaccine compositions of the present invention. As will be readily apparent, the diseases caused by certain members of the group, especially parainfluenza, measles and mumps, are very widespread in humans, especially among children, and may be responsible for causing unusually harmful symptoms and/or side effects in afflicted individuals. For example, parainfluenza-type 3 virus infects nearly all the children in the U.S. by the age of 6 years.

The F glycoprotein is known, in at least parinfluenza, to be potentially separable into subunits. For the purposes of the present specification and claims, any reference to an F glycoprotein is intended to refer to either the F glycoprotein as a whole, or its individual subunits, all of which may be detergent-solubilized.

The present compositions are relatively simple to prepare. The virus of interest is first cultured in a suitable host cell culture. The cells may be any host cells which are known to support viral growth, and these and the associated virus culture conditions will be well known to one skilled in the art. Among the commonly used cell lines for human virus are vero cells, (African green monkey kidney), baby hamster kidney, (BHK) and LLC-MK$_2$ (rhesus monkey kidney), but many other types are also acceptable for different viruses, all of which will be familiar to the skilled artisan. The viruses are allowed to propagate for a short period of time, usually until cytopathic changes begin to be observed in the culture cells; at this point the virus may be harvested from the culture fluid. Alternatively, the viruses may be grown in embryonated hen's or duck's eggs. The virus is then pelleted from the culture fluid, and further purified, to remove any associated cellular debris, by known separation techniques. Such techniques are well known to the experienced microbiologist.

The purified virions are then solubilized utilizing a dialyzable detergent. The characteristics of the detergent must be such that the glycoprotein and lipid are solubilized and that the detergent may be easily dialyzed. By "easily dialyzed" is meant that detergent removal can be accomplished in a matter of days, rather than weeks. Detergents fitting this category may be nonionic, cationic or anionic, and will be readily known to those skilled in the art. Among the possible choices are cholate or octyl-D-glucoside. Although a number of the commonly used detergents, such as Triton X-100, may be theoretically dialyzable, the period of time required to achieve the removal of detergent by dialysis is so long that they are impractical to use. It must be recalled here that, unlike the situation with known glycoprotein preparations in which it is thought to be desirable to remove lipid from the solubilized product, the present preparations require that the lipid remain in the final preparation. It is therefore a primary consideration that the detergent used is readily dialyzable, so that the detergent alone will be removed during the process of preparation. Following solubilization, the insoluble nucleocapsids may be removed from the solution by centrifugation or other appropriate means. The soluble product, following dialysis, is detergent free and comprises the desired antigenic components, HN and F glycoproteins. other proteins does not affect the antigenic activity of the principle antigenic components, and they may be present in trace amounts in the final composition with no ill effects. Further purification of the glycoproteins may be achieved by affinity chromatography using monoclonal antibodies to HN and F; this is discussed in more detail below. Also present in the final dialysate is a significant amount of endogenous viral lipid, which is an important component of the final vaccine composition. Upon removal of the detergent from the glycoproteins and lipids vesicles form which act together to produce the desired immunogenic effect. These glycoprotein-lipid complexes form the active subunits which constitute the immunogenic ingredient of the final vaccine composition.

As they occur naturally in the viral envelope, the HN and F proteins have been found to exist in differing proportions. In human PI-3, for example, the HN glycoprotein is present in the viral envelope in an amount about 4 times that of F glycoprotein. The F glycoprotein, although naturally present in small amounts in the virus, has been shown to be extremely important in the generation of immunity in the exposed individual. The development of complete immunity requires the exposure to a significant amount of the F protein. A vaccine preparation prepared in accordance with the foregoing procedure will provide sufficient amounts of F glycoprotein to confer complete immunity, provided adequate dosages of the envelope proteins as isolated are administered. This is discussed in more detail below. However, although not necessary, it may in some cases be desirable to enrich the subunit components with additional purified F glycoprotein, thus enabling the use of lower dosages of the vaccine. In an F-enriched vaccine, sufficient purified F glycoprotein may be added to bring the proportions of HN:F within the range of about 1:1.

In connection with the desirability of being able to isolate and/or purify the F or HN glycoproteins for further use, monoclonal antibodies to each of the antigens are easily prepared. The preparation of hybridoma cell lines derived by fusing an immortal cell line and lymphocytes sensitized against the immunogenic preparation can be done by techniques which are well known to those who are skilled in the art. (See, for example, Douillard, J-Y. and Hoffman, T., "Basic Facts About Hybridomas," in: Compendium of Immunology Vol. II, L. Schwartz (Ed.) (1981); Kohler, G. and Milstein, C., Nature 256, 495-497 (1975); European Journal of Immunology, Volume 6 pp. 511-519 (1976), Koprowski et al, U.S. Pat. No. 4,172,124, Koprowski et al, U.S. Pat. No. 4,196,265 and Wands, U.S. Pat. No. 4,271,145, the teachings of which are herein incorporated by reference.)

The choice of animal is dependent on the availability of appropriate immortal lines capable of fusing with lymphocytes thereof. Mouse and rat have been the animals of choice in hybridoma technology, and are preferably used. Humans can also be utilized as sources for sensitized lymphocytes if appropriate immortalized human (or nonhuman) cell lines can be carried out until the animal serum is positive to the immunogenic preparation. For the purpose of the present invention, the animal may be injected with either purified virions or viral protein from a disrupted viral envelope. Usually the injecting material is emulsified in Freund's complete adjuvant. The detection of antibodies can be carried out by testing the antisera with appropriately labeled antigen. Lymphocytes can be obtained by removing the spleen or lymph nodes of sensitized animals in a sterile fashion and carrying out fusion. Alternately, lymphocytes can be stimulated or immunized in vitro.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: MPC$_{11}$-X45-6TG, P3-NS1-1-Ag4-1, P3-X63-Ag8, or mutants thereof such as X63-Ag8.653,SP2-0-Ag14 (all BALB/C derived), Y3-'Agl.2.3 (rat), and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1,000 to 6,000. It gives best results when diluted to about 50% w/w in saline or serum-free medium. Exposure to PEG at 37° C. for about 30 seconds is preferred in the present case, utilizing murine cells. Extremes of temperature should be avoided and preincubation of each component of the fusion system at 37° C. prior to fusion gives optimum results. The ratio between lymphocytes and malignant cells should be optimized to avoid cell fusion among spleen cells. Myeloma/lymphocyte ratios ranging from 1:1 to 1:10 give good results.

The successfully fused cells can be separated from the myeloma line by any technique available to the art. The most common and preferred method is to choose a malignant line which is Hypoxanthine Guanine Phosphoribosyl Transferase (HGPRT) deficient, which will not grow in an aminopterincontaining medium because of its inability to synthesize purines from thymidine and hypoxanthine. The selection medium used to allow only growth of hybrids is generally composed of hypoxanthine $1 \times 10^{-4}$, aminopterine $1 \times 10^{-5}$M, and thymidine $3 \times 10^{-5}$M, commonly known as the HAT medium. The fusion mixture can be grown in the HAT-containing culture medium immediately after the fusion or 24 hours later. The feeding schedules usually entail maintainance in HAT medium for two weeks and then feeding with either regular culture medium or hypoxanthine, thymidine containing medium.

The growing colonies are then tested for the presence of antibodies that recognize the antigenic preparation. Detection of hybridoma antibodies can be performed using assays where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 days of cell growth in selected medium. Cloning can be performed by cell limiting dilution in fluid phase or by directly selecting single cells growing in semi-solid agarose. For limiting dilution, cell spensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals with inflammatory ascites. Antibody containing ascites can be harvested 8-12 days after intraperitoneal injection. The ascites contain a higher concentration of antibodies but include both monoclonal and immunoglobulins from the inflammatory ascites.

The above-techniques have been particularly successful in yielding hybridomas which secrete antibodies specific for human PI-3 HN or F glycoproteins. The monoclonal antibodies so produced are tested to ascertain their antibody specificity by immune fluorescence hemagglutination inhibition, (HI) neuraminidase inhibition (NI) neutralization of infectivity (NT), and immune precipitation tests, all of which are techniques well known in the art. A significant reactivity in HI, NI and NT tests identifies an antibody directed to the HN glycoprotein. Neutralization of virus infectivity and utilization of virus-induced cell fusion at lower dilutions, without a significant HI or NI titer indicates an antibody against the F glycoprotein. Although the patterns of reactivity in the above tests may vary somewhat from antibody to antibody, a number of monoclonal antibodies specific for either the HN or the F-glycoprotein have been obtained and identified by the above-described procedures.

The isotype of the antibodies is determined by ELISA using goat anti-mouse isotype specific antibodies coupled to alkaline phosphatase (Southern Biotechnology Associates, Inc., Birmingham, Ala.). While all the identified antibodies have a satisfactory level of reactivity with their specific glycoprotein, particularly effective antibodies are produced by the hybridomas designated 13-5-9-6-2 and 9-4-3, their antibodies being specific in the HN and F glycoproteins respectively.

The monoclonal antibodies as noted above, can be usefully employed for affinity purification of the HN and F glycoproteins. Affinity chromatography, a method of fractionation which exploits the biospecific binding of a particular molecule to a second molecule, can be used very profitably with the present monoclonal antibodies to produce a highly purified antigen. Generally speaking, in this procedure the monoclonal antibody is immobilized as an affinity matrix, and a solution containing the desired antigen is contacted with the immobilized antibody; the high specificity of the antibody for the antigen allows selective extraction of the antigen, while the remaining unwanted components of the solution simply pass through the column. The bound antigen is then eluted in isolation from the column. The techniques for the processes of immobilization and elution are well known in the art, and any number of these are contemplated as suitable for the present purpose. A summary of commonly used techniques is found in J. W. Goding, *Monoclonal Antibodies: Principles and Practice*, Chap. 6, Academic Press, 1983.

It will be apparent to one skilled in the related arts that the use of the F glycoprotein purified as described above is not limited to its addition to the solubilized glycoprotein-lipid subunit vaccine as a source of enrichment of this glycoprotein. In fact, affinity purified HN and F glycoproteins are also suitable components for a vaccine preparation. Because these elements will have been isolated and purified separately, they may then be combined, in an appropriate diluent vehicle or carrier, in the required proportions. Ratios of about 4:1 to about 1:1 (or more) HN to F can be employed to yield a significant protective effect. The F glycoprotein may also be used alone, because of its potent effect in inducing immunity.

The monoclonal antibodies of the present invention may also be used for purposes other than glycoprotein purification. For example, the antibodies are also useful as reagents in diagnostic testing for the presence of the parainfluenza virus in a patient suspected of being affected with the disease. Probably even more important, however, is the use of the antibodies as part of a passive immunization program i.e., using the antibodies as a substitute for the body's own natural immune response to the viral antigens. The monoclonal antibodies in vaccine form thus provide an immediate source of protection without the necessity of waiting for the patient's own antibody response to act.

As has been discussed previously, the presence of lipid with the glycoprotein in a vaccine appears to have an unexpected beneficiating effect on the stimulation of the host's body's immune response. Although the reason why this occurs is unknown, it is possible that the presence of these natural lipids acts as an adjuvant, thus enhancing the antigenic effect of the glycoprotein. The endogenous lipid present in the viral envelope is sufficient, when simultaneously extracted with the glycoprotein by the earlier described procedure, to evoke an adequate protective level of antibody production. However, if the vaccine is to be prepared from purified, isolated glycoprotein, it will be desirable to add lipid from an external source in order to obtain the same result seen with the unpurified preparation having naturally occurring lipid. This essentially has the effect of reconstituting the original protein-lipid membrane structure; upon the addition of the lipid, it will spontaneously form vesicles with the protein, to mimic the product obtained with the simple solubilization of the viral envelope followed by dialysis. It is a relatively simple matter to form these vesicles by addition of the lipid to the glycoproteins. Substantially all that is required is dissolving the lipid in a dialyzable detergent solution containing the glycoproteins, and dialyzing the solution as described previously in the solubilization procedure. In this manner, not only is it possible to prepare vesicles by combining purified protein with exogenous lipid, but it is also possible, by addition of lipid to the solubilized protein-lipid preparation, to amplify the effect of the endogenous lipid by increasing the natural lipid:protein ratio. Virtually any source of lipid is acceptable for the reconstitution of the vesicular structures. Among the lipids contemplated as useful in the present vaccine are phospholipids, such are found in lecithin, cephalin and sphingomycetin. Particularly preferred is lecithin, especially egg lecithin, a phosphatidyl choline.

The compositions of the present invention are typically administered parenterally, e.g., subcutaneously intraperitoneally, intramuscularly, or intravenously. The antigenic complex may be administered simply in combination with pharmaceutically acceptable carrier such as water, buffered saline, ethanol, polyol (for example, glycerol, propylene glycol, liquid polyethylene glycol and the like) suitable mixtures thereof, and vegetable oils. Where appropriate, the action of contaminating microorganisms can be prevented by various antibacterial and antifungal agents, such as parabens, chlorobutanol, phenol, sorbic acid, thimerosal, and the like. It will often be preferable to include isotonic agents, for example, glucose or sodium chloride.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the vertebrate subjects to be treated; each unit containing a predetermined quantity of active material calculated to produce the desired therapeutic effect in association with the required pharmaceutical carrier. The specification for the novel dosage unit forms of the invention are dictated by and directly dependent on the unique characteristics of the active material and the particular therapeutic effect to be achieved, and it is within the skill of the physician to determine the dose appropriate for the subject involved. Generally, when administering a composition comprising the HN and F antigens of the virus, a dosage of about 40–200 μg is satisfactory for producing the desired immune response. The dosage range is of course varied depending on the proportions of F antigen present in the mixture; in a case in which the composition contains nearly equal amounts of HN and F, the dosage is preferably in the lower end of the range, whereas, when it is not feasible to prepare a composition with larger quantities of F present, it is necessary to administer higher doses.

The glycoprotein-lipid containing viruses are responsible for causing disease in a wide variety of vertebrate hosts, and the present vaccine compositions are adaptable for treatment of any vertebrate host which is susceptible to these infections. However, the preferred vaccines of the invention, directed to prevention of parainfluenza infection, are most valuable in treatment of mammalian hosts, including man.

The present invention may be more readily understood by reference to the following non-limiting examples:

EXAMPLE 1

The following example demonstrates the process of preparing the vaccine compositions of the present invention, using human parainfluenza 3 virus.

Human parainfluenza 3 virus (strain 47885) was obtained from the Division of Research and Resources, NIH. The virus was plaque purified in Vero cells. LLC-MK$_2$ (rhesus monkey kidney), Vero (African green monkey kidney) and BHK (baby hamster kidney) cell lines were obtained from the American Type Culture Collection.

Serial ten fold dilutions of the supernatant in 200 ul volumes were inoculated on Vero cell monolayers in 40 mm diameter well plastic tissue culture dishes (Costar Plastics). After 1 h of incubation at 37° C. in a 5% $CO_2$ incubator, with intermittent agitation, dishes were washed with medium and an overlay of 3 ml of Dulbecco's medium containing 1% newborn calf serum (NCS) and 0.9% agar was added to each well, and cells were incubated at 37C for 4 days. Finally, another overlay of 3 ml Dulbecco's medium containing 1% NCS and 0.9% agar and 0.005% neutral red was added and the dishes further incubated for 12 h before counting plaques.

Confluent monolayers of LLC-MK$_2$ cells were infected at a concentration of 1 plaque forming unit/cell. After absorption for 1 hr at 37° C., cells were incubated in Dulbecco's medium containing 2% heat inactivated NCS at 37° C. in a 5% $CO_2$ incubator.

For radiolabeling with amino acid precursors, the virus was grown in leucine or methionine-free Eagle's medium containing 2% NCS and 10 uCi/ml of $^3$H-leucine (Amersham, Sp. activity 64.6 Ci/mmol) or $^{35}$S-methionine (Amersham, Sp. activity 1345 Ci/mmol). Sugar labeling was done in serum-free Eagle's medium containing 10 uCi/ml of $^3$H-glucosamine hydrochloride (Amersham, Sp. activity 39 uCi/m mol). The virus was harvested from the culture fluid at 48 h postinfection, when a moderate cytopathic effect developed. The culture fluid was first clarified from cellular debris by low speed centrifugation (5,000×g, 30 min at 4° C.) and virus was pelleted by high speed centrifugation (143,000×g, 45 min at 4° C). Pellets were resuspended in phosphate-buffered saline (PBS) and the virus was purified by centrifugation (300,000×g, 1 h at 4° C.) through a 30–60% discontinuous sucrose cushion. The virus band was collected from the interface, diluted with PBS, and pelleted by high speed centrifugation (300,000×g, 30 min at 4° C.).

Purified virions were suspended in 0.1M Tris-CHl, 0.1 M NaCl, pH 7.6 containing 2% octylglucoside (Sigma Chemical Co., St. Louis, Mo.) and allowed to stand at room temperature for 30 min. The insoluble nucleocapsid portion was removed by centrifugation (300,000×g, 30 min at 4° C.). The supernatant, containing detergent soluble envelope constituents, was dialysed against three changes of 0.01M Tris-HCl, 0.01 M NaCl, pH 7.6 for 48 h at 4° C. The protein content and hemagglutination titer of the dialysis were determined. The protein content of samples was determined by using a commercially prepared dye reagent (Bio-Rad Laboratories, Richmond, CA) following the method of Bradford Anal. Biochem. 72: 248–54, 1976). The protein component of the viral envelope, in addition to the HN and F glycoproteins, was found to consist of other polypeptides of varying molecular weight. These are designated as L, P, NP, M, actin, and an unidentical 22k polypeptide.

The soluble and insoluble fractions after treatment of $^3$H-leucine-labeled virions with octylglucoside were analyzed by SDS-PAGE as shown in FIG. 1. It is apparent that the detergent could solubilize viral HN, F, and presumably M and actin to some extent (lane 3). On the other hand, the nucleocapsid associated proteins, NP, P and L remained in the detergent insoluble portion. Treatment of $^3$H-glucosamine labeled virions with the detergent confirmed the solubilization of the HN and F glycoproteins. Approximately one third of the total virus protein could be recovered in the detergent-soluble portion, and the material showed a significant HA titer (1:320). In contrast, formalin-inactivated whole virus preparations had much lower HA titers (1:8).

EXAMPLE 2

This Example shows the effectiveness of the present vaccine in inducing an immune response in a mammalian host:

Female hamsters, four weeks old, each weighing about 65 gm, were procured from Charles River Breeding Labs. Animals were test bled from the orbital sinus before immunization to determine the possible presence of preexisting antibody.

Two types of vaccine compositions were prepared: one contained as its active ingredient the solubilized envelope proteins, as described in Example 1; the second contained formalin inactivated virus, prepared by incubating a purified virus suspension in 0.25% formaldehyde at 37%C overnight. The inactivated virus suspension was dialyzed against 0.01M Tris-HCl, 0.01M NaCl, pH 7.6 overnight to remove the formaldehyde. Compositions of varying concentration, for each of the two compositions were prepared and administered to the hamsters as follows.

Groups of animals were immunized simultaneously with detergent soluble viral envelope proteins or formalin inactivated whole virus proteins. Serum samples from immunized animals were collected by weekly bleeding from the orbital sinus. Sera were inactivated at 56° C. for 30 minutes and tested for antibody response to viral glycoproteins. Animals immunized with the viral envelope preparation as described in Example 1, showed elevated antibody response to the HN glycoprotein in an HI test (FIG. 2); other groups of animals immunized with formalin-inactivated whole virus proteins showed lower HI titers. Although the antibody response varied with the vaccinating dose, both groups of animals had peak responses by the second week after immunization and the level of antibody to the HN glycoprotein persisted up to the 5th week.

The serum neutralizing antibody response of immunized hamsters also varied with the dose of antigen, and the highest dose of envelope proteins (80 μg) induced a prolonged response (FIG. 3). Animals immunized with 40 μg of envelope proteins or 240 μg of formalin-inactivated viral proteins showed a gradual rise in antibody response up to the 4th week after immunization, while lower doses did not induce as high a titer.

Immunized hamster sera collected at weekly intervals were also tested to evaluate the antibody response to viral glycoproteins by immune precipation with $^3$H-glucosamine labeled virus (FIG. 4). An antibody response to the HN glycoprotein was observed from the 2nd week after immunization, even with the lowest dose of the two antigen preparations. Sera from hamsters immunized with the highest dose of viral envelope proteins or formalininactivated virus proteins also showed a detectable antibody response to the F glycoprotein by the 3rd week after immunization, while animals immunized with lower doses of antigens showed no antibody response to this glycoprotein.

Hamster sera also showed significant differences when tested for inhibition of cell fusion. Virus-infected BHK cells did not show a demonstrable cytopathic effect following incubation with sera (1:20) from hamsters immunized with envelope glycoprotein preparations. In contrast, large syncytia were observed in cultures treated with sera from other groups of animals, immunized with formalin-inactivated virus.

EXAMPLE 3

This Example shows the protective effect of the envelope glycoprotein vaccine with exposure to subsequent challenge with active virus.

Hamsters were anaesthesized by intramuscular injection (0.25 ml/100 gm) of a mixture of ketamine hydrochloride (87 mg/ml) (Bristol Laboratories, New York) and xylazine (13 mg/ml) (Haver-Lockhart, Shawnee, Kansas) and infected intranasally with virions in 100 μl Dulbecco's medium containing 1% BSA. During inoculation the tongue of the animal was pulled out to avoid swallowing and virus administered slowly in aliquots through the nostrils.

Hamsters were sacrificed by using a lethal dose of ketamine hydrochloride ylazine. When the animals were still living, they were bled out from the axilla until death. The thoracic cavity was opened and bronchial washing was first collected by instilling and aspirating 1 ml of Dulbecco's medium containing 1% BSA through the upper portion of the trachea by a syringe and 16½ gauge needle. Lungs and trachea were separated, suspended in the above medium and stored frozen at −70° C. until assayed. Tissue suspensions were thawed, cut into small pieces and homogenized in Dounce tissue grinder (Wheaton Scientific, NJ). The homogenized tissue suspension was centrifuged at 1,500×g for 15 min to discard particulate material.

The minimum infective dose required to establish infection in hamsters, as determined by recovery of virus from lungs, was determined to $10^3$ p.f.u. Replication of the virus in hamsters infected with a dose of $10^5$ p.f.u. is shown in FIG. 5. After 2 h of infection, no infective virus was recovered in the bronchial wash, trachea or lung homogenate. Low recovery was observed from trachea only on the day after infection and similar titers of virus were found in the bronchial wash up to the third day of infection. The virus was recovered in the lungs of infected animals by the day after infection and titers increased up to $3 \times 10^4$/gm on the second day. The titer then decreased slightly on the third and fourth day, after which virus could not be detected.

The recovery of virus from immunized animals and controls on the third day after challenge infection is shown in Table 1. Similar virus titers were obtained from hamsters immunized with the lowest dose of formalin-inactivated virus protein (60 µg) and unimmunized control animals. However, animals immunized with 20 µg or 40 µg of the envelope proteins showed reduced virus titers in their lungs. Similar virus titers were recovered from animals immunized with 120 or 240 µg of formalin-inactivated virus protein. Animals immunized with a dose of 80 µg of envelope proteins did not show any detectable virus in their lungs after challenge infection. The lung homogenates from this group of animals were further tested by plaque assay with higher volume inocula (0.6 ml) in large tissue culture dishes (100 mm) to detect lower levels of infective virus. Two out of nine animals demonstrated the presence of virus at very low levels ($3.3 \times 10^1$ and $4.4 \times 10^1$ p.f.u./gm) with the higher volume inoculum, and no infectivity was detected in the remaining animals. These results indicate that immunization with the envelope glycoproteins induced a dose-dependent protective immune response to challenge infection in hamsters. On the other hand, immunization with formalin-inactivated virus reduced the titers of infective virus but did not confer complete protection even at the highest dose tested.

TABLE 1

Challenge of immunized hamsters with infective virus[a]

| Immunizing antigen | Virus recovery (p.f.u./gm) from lungs after 72 h of challenge infection[b] |
|---|---|
| Unimmunized control hamsters | $1.1 \times 10^4$ |
| 60 ug inactivated whole virus proteins | $4.2 \times 10^3$ |
| 120 ug inactivated whole virus proteins | $3.0 \times 10^2$ |
| 240 ug inactivated whole virus proteins | $2.9 \times 10^2$ |
| 20 ug envelope proteins | $2.5 \times 10^2$ |
| 40 ug envelope proteins | $2.3 \times 10^2$ |
| 80 ug envelope proteins | $<1 \times 10^1$ |

[a]$10^5$ pfu were inoculated intranasally
[b]Each value represents the geometric mean titer from nine animals immunized with each dose of envelope proteins or inactivated whole virus proteins.

Groups of animals immunized with the highest dose of antigen, and showing a serum antibody response to both viral glycoproteins, were evaluated for the presence of antiviral antibody in their bronchial washings after challenge infection. Bronchial washings from both the immunized groups were found to have reactivity up to a dilution of 1/100 in ELISA. The bronchial wash from unimmunized control hamsters after challenge infection did not show any reactivity. The presence of IgG antibody specifically against viral envelope glycoproteins in the bronchial wash was further determined by indirect immunofluorescence with unfixed virus-infected LLC-MK$_2$ cells, and goat anti-hamster IgG FITC conjugate. The bronchial washes from both groups of immunized animals were found to be positive for immunoflourescence, unlike the unimmunized control.

Bronchial washings were also examined by immune precipitation experiments with $^3$H-glucosamine labeled virus. Animals from both the immunized groups showed the presence of antibody specific for the HN and F glycoproteins of the virus while unimmunized challenged animals failed to show any demonstrable antibody against these two glycoproteins.

EXAMPLE 4

This Example demonstrates the procedure for preparation of monoclonal antibodies to the HN and F glycoproteins of human Parainfluenza 3 virus.

BALB/c mice were immunized with virus disrupted by repeated freeze-thaws (ten times). A total of five intramuscular immunizations with 10 µg of viral protein each were administered at 3 day intervals. The first immunization contained Freund's complete adjuvant. Lymph node cells were fused with a non-secreting myeloma cell line ($\times$63? Ag 8.653) using polyethylene glycol 4,000, three days after the last injection. Screening of the culture fluids was initially done by ELISA and cloning was performed by limiting dilution in microtiter plates. Fused cells were cultured in RPMI 1640 medium containing hypoxanthine, aminopterin and thymidine. Culture fluids from growing colonies were initially screened by ELISA using disrupted virions as antigen. Cultures showing reactivity to viral antigens were cloned by limiting dilution in microtiter plates. Culture fluids from cloned cells were further tested to ascertain their antibody specificity by immunofluorescence, hemagglutination inhibition, neuraminidase inhibition, neutralization of infectivity and immune precipitation tests. The isotype was determined by ELISA using goat anti-mouse isotype specific antibodies coupled to alkaline phosphatase (Southern Biotechnology Associates, Inc., Birmingham, Ala.). Hybridoma cells were inoculated intraperitoneally into mice for large scale preparation of antibodies from ascites fluid. A total of twenty-three monoclonal antibodies were obtained of which twenty were determined to be against HN and one against F.

Monoclonal antibody specificity was evaluated by determination of hemagglutination inhibition (HI), neuraminidase inhibition (NI), immunofluorescence with fixed and unfixed virus infected cells and immune precipitation with radiolabelled virus infected lysate. The protocol followed for each of these assays is oulined below:

Hemagglutination solution (HI): Sera were created with sodium mataperiodate to destroy possible sialic acid containing inhibitors. Serial two-fold dilutions of test serum or monoclonal antibodies (50 µl) were made in PBS (without $Ca^{+2}$ and $Mg^{+2}$) in 96 wells microtiter plate. Eight hemagglutination units of virus suspension (50 µl) was then added to each well and incubated at 37° C. for 1 h. Then 100 µl of a 0.3% suspension of sheep erythrocytes in PBS (without $Ca^{+2}$ and $Mg^{+2}$) was added to each well and the plate was incubated at 4° C. for about 2 h until a clear button or hemagglutination was observed with negative and positive controls, respectively. The HI titer is expressed as the reciprocal of the highest dilution of serum which completely inhibited hemagglutination.

(ii) Neuraminidase inhibition (NI): Serial two-fold dilutions (50 μl) of hybridoma ascites fluid in 0.2 M Na-acetate buffer, pH 5.5, were mixed with equal volume of virus suspension (400 μg/ml) and incubated at 37° C. for 1 h. Then 0.1 ml bovine fetuin (type IV) (15 mg/ml) (Sigma Chemical Co., St. Louis, Mo.) dissolved in the same buffer was added and the reaction mixture was incubated at 37° C. overnight. Released neuraminic acid was determined by the method of Warren. Reaction mixture without ascites fluid were used as the controls. The neuraminidase titer is expressed as the reciprocal of the highest dilution at which 50% inhibition occurred.

(iii) Neutralization of infectivity: Serial two-fold dilutions of test sera or hybridoma supernatants were mixed with an equal volume of virus suspension (100 p.f.u.) in Dulbecco's medium containing 1% BSA and incubated at 37%C for 1 h. After incubation, 0.2 ml of the mixture was added to Vero cell monolayers in tissue culture dishes and the procedure described for plaque assay was followed. The neutralization titer was expressed as the highest dilution serum which inhibited plaque formation by 50%.

(iv) Immune precipation: Bronchial wash (400 μl), test serum or monoclonal antibody (20 μl) was diluted to 1 ml in lysis buffer and extensively adsorbed with an acetone powder of LLC-MK$_2$ cells. The composition of the lysis buffer was 0.05M Tris-HCl, pH 7.4, 0.15M NaCl, 0.001 M EDTA, 1% sodium deoxycholate, 1% Triton Z-100 and 0.1% SDS. The cellular debris was removed by centrifugation. The supernatant portion was mixed with $^{35}$S-methionine-labeled virus-infected LLC-MK$_2$ cell lysate or purified $^3$H-glucosamine-labeled virus and incubated overnight at 4° C. in a rotary mixer. A predetermined quantity of Protein A-agarose (Pierce Chemical Company, U.S.A.) was added to the antigen-antibody mixture and incubated for 2 h in a similar condition. The immunosorbent beads were collected by centrifugation and washed four times with cold lysis buffer. The immune precipitates were finally analyzed by SDS-PAGE followed by autoradiography or fluorography.

(v) Inhibition of virus-induced cell fusion: Confluent monolayers of BHK cells were grown in multiwell tissue culture dishes and infected with virus as described earlier. After 6 h of infection, cells were washed with culture medium and replaced with fresh medium containing two-fold dilutions of preimmune sera or test sera (heat activated at 56° C. for 30 min.) and incubation was continued for another 30 h. Infected cell monolayers were washed with PBS and fixed with methanol. Cell monolayers were stained with Giemsa and examined with a Nikon phase-contrast microscope.

(vi) Enzyme-linked immunosorbent assay (ELISA): Dynatech polyvinyl plates were coated with 1 μg protein/well or purified freeze-thaw disrupted virions in 100 μl of borate-buffered saline, pH 8.3 by incubation overnight at 4° C. After three washings with physiological saline, the plates were filled with 1% bovine serum albumin (Sigma Chemical Co., St, Louis, MO) in the above buffer for 1 h at room temperature to block the (extensively adsorbed with acetone dried powder of LLC-MK$_2$ cells) were added to the antigen coated wells and incubated for 1 h at 37° C. The plates were washed three times and an appropriate dilution (determined by checker board titration) of goat anti-hamster IgG (Cappel Laboratories, Philadelphia, PA) was added to each well and incubated for another 1 h at 37° C. The plates were washed again and 100 μl of an appropriate dilution of rabbit anti-goat Ig conjugated to alkaline phosphatase (Sigma Chem. Co., St. Louis, Mo.) was added to each well and incubated for another 1 h at 37° C. Finally, plates were washed and 100 μl of p-nitrophenyl phosphate (Sigma Chem. Co., St. Louis, Mo.) in 10% diethanolamine buffer, pH 9.6 containing 0.5M MgCl$_2$ was added to each well. After incubation for 30 min, the color reaction was read at 405 nm with a spectrophotometer (Titertek Multiskan MC, Flow Laboratories).

(vii) Immunofluorescence (IF): Confluent monolayers of LLC-MK$_2$ cells were grown on coverslips and infected with virus as described above. At 24 h post-infection, cells were washed with PBS. Test samples were applied to the infected cells and incubated for 15 min at room temperature. After washing with PBS, goat anti-hamster IgG conjugated to fluorescein isothiocyanate (Cappel Laboratories, Philadelphia, Pa.) was added and incubated for anothr 15 min. After extensive washing with PBS, the coverslips were mounted on microscope slides using a solution of glycerol in PBS and observed with Nikon fluorescence microscope.

As noted, twenty of the twenty-three antibodies were directed to HN glycoprotein, based on significant reactivity in HI, NI abd NT tests. The reactiveness of these antibodies is outlined in Table 2. The antibody from clone 9-4.3 showed no significant HI or NI titer, but was capable of neutralizing virus infectivity and inhibited virus-induced cell fusion at lower dilution, indicating it is specific against the F glycoprotein. These specificities are further corroborated by the reactivities with isolated polypeptides previously identified as HN and F components of the viral envelope.

TABLE 2

REACTIVITY OF MONOCLONAL ANTIBODIES WITH THE HOMOLOGOUS STRAIN OF HUMAN P13 VIRUS IN HEMAGGLUTINATION INHIBITION (HI), NEURAMINIDASE INHIBITION (NI) AND PLAQUE NEUTRALIZATION (NT) TESTS

| Antibody Group | Antibody+ Clone Designation | Isotype | HI titer | NI titer | NT titer* |
|---|---|---|---|---|---|
| I | B.1.1 | IgG2a(K) | 320,000 | 16 | 51,200 |
|   | 7.12.3 | IgG2a(K) | 65,600 | 32 | 2,000,000 |
|   | 13.5.9.6.2a | IgG2b(K) | 40,000 | 100 | 3,200 |
|   | C.4.3 | IgG2a(K) | 1,280,000 | 100 | 204,800 |
|   | 7.24.3 | IgG1(K) | 65,600 | 512 | 2,000,000 |
|   | 2.14.1 | IgG2a(K) | 131,200 | 1,000 | 40,000 |
| II | B.4.5 | IgM(K) | 16 | <4 | 1,600 |
|   | 2.2.3.5 | IgG3(K) | 32 | <4 | 200 |
|   | 14.11.6.2 | IgG1(K) | 5,000 | <4 | 1,600 |
|   | 9.1.6.2 | IgG1(K) | 32,800 | <4 | 25,600 |
|   | 3.16.1 | IgM(K) | 131,200 | <4 | 100,000,000 |
|   | 2.2.5.1.2 | IgG1(K) | 8,200 | <4 | 10,000 |
|   | 4.5.2 | IgG2a(K) | 524,800 | <4 | 4,000 |
|   | 9.1.1 | IgG1(K) | 40,000 | <4 | 6,400 |
|   | 2.4.4 | IgG1(K) | 4,096 | <4 | 20,000 |
| III | 9.13.1 | IgG2a(K) | <4 | 32 | 400 |
| IV | 7.14.2 | IgG1(K) | 1,024 | <4 | 16 |
|   | 4.4.4 | IgG2b(K) | 65,600 | <4 | 8 |
| V | 5.4.8 | IgM(K) | <8 | <4 | <8 |
|   | 3.8.1 | IgG1(K) | <8 | <4 | <4 |

+All these antibodies showed immunofluorescence with unfixed virus infected cells and could specifically precipitate the HN polypeptide in immune precipitation experiments.
*Plaque neutralization titers were determined following the methodology described previously (Ray et al., 1985).

We claim:

1. A vaccine composition useful in prevention of virus-caused disease comprising, as an active agent, an immunogenically effective amount of at least one immunogenic (F) fushion viral envelope glycoprotein from said virus complexed with a lipid, and a pharmaceutically acceptable carrier.

2. A vaccine composition useful in prevention of virus-caused disease comprising, as an active agent, an immunogenically effective amount of at least one immunogenic (HN) receptor-binding viral envelope glycoprotein from said virus complexed with a lipid, and a pharmaceutically acceptable carrier.

3. A vaccine composition useful in prevention of virus-caused disease comprising, as an active agent, an immunogenically effective amount of at least one immunogenic (F) fushion viral envelope glycoprotein and at least one immunogenic (HN) receptor-binding viral envelope glycoprotein from said virus complexed with a lipid, and a pharmaceutically acceptable carrier.

4. The composition of claim 1, 2 or 3 wherein the virus is a glycoprotein and lipid containing virus.

5. The composition of claim 4 wherein the virus is selected from the group consisting of herpes virus, influenza virus, rabies virus, paramyxoviruses, human T-cell lymphotropic viruses.

6. The composition of claim 5 wherein the virus is a paramyxovirus.

7. The composition of claim 5 wherein the virus is a parainfluenza virus.

8. The composition of claim 7 wherein the virus is a parainfluenza 3 virus.

9. The composition of claim 8 wherein the virus is human parainfluenza 3 virus.

10. The composition of claim 1, 2 or 3 wherein both the glycoprotein and lipid are derived from the viral envelope.

11. The composition of claim 1, 2 or 3 wherein the lipid is derived from a source other than the viral envelope.

12. The composition of claim 9 which further comprises lipid from a source other than the viral envelope.

13. The composition of claim 10 wherein the lipid is lecithin.

14. The composition of claim 13 wherein the lipid is egg lecithin.

15. The composition of claim 11 wherein the lipid is lecithin.

16. The composition of claim 14 wherein the lipid is egg lecithin.

17. The composition of claim 1 in unit dosage form.

18. A vaccine composition prepared by dialyzing a solution comprising a dialyzable detergent, at least one solublizied fusion glycoprotein, and solubilized lipid, so that a gylcoprotein lipid complex is formed, and combining said complex with a pharmaceutically acceptable carrier.

19. A method of preventing virus-caused disease which comprises administering to a vetebrate an immunogenically effective amount of the composition of claim 1, 2 or 3.

* * * * *